(12) United States Patent
Riether (10) Patent No.: US 9,772,342 B2
(45) Date of Patent: *Sep. 26, 2017

(54) DISPATCHING DEVICE, SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Christian Riether, Muehltal (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/665,454

(22) Filed: Mar. 23, 2015

(65) Prior Publication Data

US 2015/0276776 A1 Oct. 1, 2015

(30) Foreign Application Priority Data

Mar. 31, 2014 (EP) .................................... 14162933

(51) Int. Cl.
| | | |
|---|---|---|
| *G01N 21/00* | (2006.01) | |
| *G01N 35/04* | (2006.01) | |
| *B65G 51/28* | (2006.01) | |
| *B65G 51/30* | (2006.01) | |
| *B65G 54/02* | (2006.01) | |

(52) U.S. Cl.
CPC ............. *G01N 35/04* (2013.01); *B65G 51/28* (2013.01); *B65G 51/30* (2013.01); *B65G 54/02* (2013.01); *G01N 2035/0401* (2013.01); *G01N 2035/0406* (2013.01); *G01N 2035/0465* (2013.01); *G01N 2035/0477* (2013.01); *G01N 2035/0481* (2013.01)

(58) Field of Classification Search
CPC ...................................................... G01N 35/02
USPC ............................. 422/63, 65; 700/228, 229
See application file for complete search history.

(56) References Cited

U.S. PATENT DOCUMENTS

| | | | |
|---|---|---|---|
| 3,273,727 A | 9/1966 | Rogers et al. | |
| 3,653,485 A | 4/1972 | Donlon | |
| 3,901,656 A | 8/1975 | Durkos et al. | |
| 4,150,666 A | 4/1979 | Brush | |
| 4,395,164 A * | 7/1983 | Beltrop ................. | B65G 51/34 406/112 |
| 4,544,068 A | 10/1985 | Cohen | |
| 4,771,237 A | 9/1988 | Daley | |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Natalia Levkovich
(74) *Attorney, Agent, or Firm* — Roche Diagnostics Operations, Inc.

(57) ABSTRACT

A dispatching device for dispatching sample containers received in respective sample container carriers from a transport surface to an external position and/or from the external position to the transport surface is presented. The dispatching device has a tube and a capsule, a conveying surface with an electromagnetic actuator being formed in the capsule. A sample distribution system with such a dispatching device and a laboratory automation system with such a sample distribution system are also presented.

9 Claims, 3 Drawing Sheets

(56) References Cited

U.S. PATENT DOCUMENTS

| | | |
|---|---|---|
| 5,120,506 A | 6/1992 | Saito et al. |
| 5,295,570 A | 3/1994 | Grechsch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A * | 4/2000 | Uchida .......... B65G 54/02 112/DIG. 2 |
| 6,062,398 A | 5/2000 | Thalmayr |
| 6,141,602 A | 10/2000 | Igarashi et al. |
| 6,151,535 A | 11/2000 | Ehlers |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,428,957 B2 | 9/2008 | Schaefer |
| 7,578,383 B2 | 8/2009 | Itoh |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,211,543 B2 | 12/2015 | Ohga et al. |
| 9,239,335 B2 | 1/2016 | Heise et al. |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 * | 12/2010 | Pedrazzini ....... G01N 35/00732 700/230 |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |

(56) References Cited

FOREIGN PATENT DOCUMENTS

| | | |
|---|---|---|
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | 01-266860 A | 10/1989 |
| JP | H02-87903 A | 3/1990 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 4/1994 |
| JP | 06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 B2 | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 | 9/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/064656 A1 | 5/2013 |
| WO | 2013/099647 A1 | 7/2013 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

DISPATCHING DEVICE, SAMPLE DISTRIBUTION SYSTEM AND LABORATORY AUTOMATION SYSTEM

CROSS-REFERENCE TO RELATED APPLICATIONS

This application claims priority to EP 14162933.7, filed Mar. 31, 2014, which is hereby incorporated by reference.

BACKGROUND

The present disclosure generally relates to a dispatching device for dispatching sample containers received in respective sample container carriers from a transport surface of a sample distribution system to an external position with respect to the transport surface and/or from the external position to the transport surface, to a sample distribution system with such a dispatching device, and to a laboratory automation system with such a sample distribution system.

Sample containers are typically elongated vessels that are open at one end and are made of usually transparent glass or plastic, which are used for storing and transporting usually liquid samples. Such samples are for example blood samples.

In the case of laboratory automation systems, it is often necessary to transport samples in sample containers to a plurality of different stations of the laboratory automation system.

Known sample distribution systems can reliably move sample container carriers between different stations or else store them for a certain time on the transport surface. It may however also be required to bring samples onto the transport surface or to dispatch samples from the transport surface to a remote device, for example a further transport surface. In the case of sample distribution systems of the generic type, this typically requires manual interventions.

Therefore, this is a need for providing a dispatching device with which sample container carriers can be dispatched from the transport surface of a sample distribution system to an external position or from the external position to the transport surface without manual interventions being necessary, for providing a sample distribution system with such a dispatching device, and for providing a laboratory automation system with such a sample distribution system.

SUMMARY

According to the present disclosure, a dispatching device for dispatching sample containers received in sample container carriers from a transport surface of a sample distribution system to an external position with respect to the transport surface and/or from the external position to the transport surface is presented. A sample container carrier can comprise at least one magnetically active element to interact with a magnetic field generated by at least one electromagnetic actuator such that a driving force is applied to the sample container carrier. The dispatching device can comprise a tube which leads from the transport surface to the external position, a capsule movable in the tube between the transport surface and the external position and comprising a conveying surface for receiving the sample container carrier, a driving unit to move the capsule in the tube between the transport surface and the external position, and at least one electromagnetic actuator arranged under the conveying surface. The at least one electromagnetic actuator applies a driving force to the sample container carrier.

In accordance with one embodiment of the present disclosure, a sample distribution system is presented. The sample distribution system can comprise a plurality of sample container carriers for receiving one or more sample containers. A sample container carrier can comprise at least one magnetically active element to interact with a magnetic field generated by at least one electromagnetic actuator such that a driving force is applied to the sample container carrier. The sample distribution system can also comprise a transport surface to carry the sample container carriers and a plurality of electromagnetic actuators arranged in a stationary manner under the transport surface. The electromagnetic actuators can move sample container carriers that are arranged on the transport surface by applying a magnetic force to the sample container carriers. The sample distribution system can also comprise a dispatching device and a control device to activate the electromagnetic actuators arranged under the transport surface such that a sample container carrier moves on the transport surface along a predeterminable path of movement, to activate the at least one electromagnetic actuator arranged under the conveying surface and/or the electromagnetic actuators arranged under the transport surface such that a sample container carrier is moved from the transport surface in the direction of the conveying surface or from the conveying surface in the direction of the transport surface, and to activate the driving unit such that the capsule is moved in the tube between the transport surface and the external position.

Accordingly, it is a feature of the embodiments of the present disclosure to provide a dispatching device with which sample container carriers can be dispatched from the transport surface of a sample distribution system to an external position or from the external position to the transport surface without manual interventions being necessary, to provide a sample distribution system with such a dispatching device, and to provide a laboratory automation system with such a sample distribution system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A dispatching device for dispatching or transporting sample containers received in respective sample container carriers from a transport surface of a sample distribution system to an external position with respect to the transport surface and/or from the external position to the transport surface is presented. A sample container carrier, which does not form part of the dispatching device and can receive one or more sample containers, can have at least one magnetically active element for interacting with a magnetic field generated by at least one electromagnetic actuator in such a way that a driving force on the sample container carrier can be brought about.

The dispatching device can have the following a tube, or pipe, which can extend from the transport surface to the external position, a capsule, which can be moved in the tube between the transport surface and the external position and which can have a conveying surface for receiving the sample container carrier, a driving unit for moving the capsule in the tube between the transport surface and the external position, and at least one electromagnetic actuator, which may also be referred to as a conveying surface actuator, arranged underneath the conveying surface and which can be designed for applying a driving force to the sample container carrier.

It can be possible by use of the dispatching device to dispatch sample container carriers with sample containers received therein from a transport surface to an external position or from the external position to the transport surface in an automated manner without particularly complex equipment. At the same time, it can be possible to dispense with both manual interventions and complex transporting systems.

By use of a sample container carrier, single or multiple samples or sample containers can be transported for example between pre-analytical, analytical and/or post-analytical stations. In particular, these may be stations of a laboratory automation system. A pre-analytical station can usually serve for the pre-processing of samples or sample containers. An analytical station may be designed for example for using a sample or part of the sample and a reagent to generate a measurable signal, on the basis of which it can be determined whether an analyte is present, and if so in what concentration. A post-analytical station can usually serve for the post-processing of samples or sample containers. By use of the dispatching device, such a pre-analytical, analytical or post-analytical station may also for example be located at the external position, while it nevertheless can accept or deliver a sample without interim manual steps.

The dispatching device may for example also be used for accepting samples in sample containers from an external sample supplier, such as for example receiving stations in a hospital. Such receiving stations may for example be used by doctors for introducing blood samples that they have taken from patients, and thereby dispatching them to the transport surface. The location at which such a receiving station is set up may then for example be referred to as an external position.

The electromagnetic actuator, preferably an electromagnet, that can be arranged underneath the conveying surface may, according to one embodiment, be electrically and mechanically connected to the capsule, and consequently also be able to move with the capsule. In other words, in this embodiment, the electromagnetic actuator can also be dispatched in the tube. However, according to an alternative embodiment, the electromagnetic actuator may also be stationary, i.e. it can remain at a specific position, which can typically be alongside the transport surface. In this case, it may be provided for example that the stationary electromagnetic actuator can be pivotable, so that, after arrival of a capsule, it can be moved under the conveying surface and, for transporting the capsule away, it can be pivoted out again from the intended area of movement of the capsule.

The driving force can be applied to the sample container carrier in order to move the sample container carrier into the capsule or move it out of it. This ideally can make possible an uninterrupted movement of a sample container carrier on the transport surface, and subsequently into the capsule or out of the capsule with a subsequent uninterrupted movement on the transport surface.

The capsule may have a closable opening for introducing the sample container carrier with a sample container received therein. This can make possible both unhindered introduction of the sample container carrier with the sample container and protection during dispatch. The tube may have a closable opening, through which the opening of the capsule can be accessible in the opened state. Such an opening can close off the tube with respect to the surroundings during dispatch, which may be advantageous for example if the capsule is moved through the tube by positive and/or negative pressure. This is explained in more detail further below.

The dispatching device may be designed for closing the sample container before or after introduction into the capsule. For this purpose, the dispatching device may have for example an actuable closure or plug, which can be pressed onto the sample container in the capsule by an actuator, for example in the form of a spring. In this way, it can be advantageously possible to prevent leaking of the sample from the sample container. In particular, leaking of the sample can even be avoided if the sample container is for example tipped over during dispatch.

The dispatching device may have a checking device, to be precise for checking whether a sample container is closed before introduction into the capsule. In this way it can be possible to avoid sample containers that are not closed being introduced into the capsule and dispatched, which may lead to the sample leaking if they are for example correspondingly tipped over, as the case may be.

The capsule may have a holding device, which can be designed for fixing the sample container carrier with the sample container in the capsule. By use of such a holding device, tipping over of the sample container carrier and/or the sample container in relation to the capsule during dispatch can be avoided. Furthermore, uncontrolled movements of the sample container carrier and/or of the sample container in the capsule during dispatch can be avoided, which for example can prevent samples from leaking or the sample container being damaged during dispatch.

The capsule may have a longitudinal direction extending transversely in relation to the conveying surface, the capsule moving in the tube with the longitudinal direction of the capsule remaining largely parallel to a longitudinal extent of the tube. This can correspond to a typical embodiment of a pneumatic dispatch system. It can consequently be possible for example in the embodiment to fall back on known components for forming a pneumatic dispatch system.

According to one embodiment, the capsule can have a plurality of conveying surfaces, at least one electromagnetic actuator arranged under a conveying surface, and the capsule further having device for bringing one of the conveying surfaces up to a specific position that can be suitable for loading and/or unloading. Multiple sample container carriers with sample containers can be dispatched by just one dispatching operation. The device for bringing one of the conveying surfaces up to a specific position allows a specific conveying surface to be loaded and/or unloaded to be brought up to the transport surface in such a way that the loading and/or unloading can be possible.

The plurality of conveying surfaces may for example be arranged along a circle and may be rotatable, for example by an electric motor. Such an embodiment may be formed in a way similar to the magazine of a revolver.

The provision of electromagnetic actuators under the plurality of conveying surfaces may take place for example in such a way that under each conveying surface there can be an assigned electromagnetic actuator, which can move along rigidly with the conveying surface and for example can also turn along with it. Alternatively, a single electromagnetic actuator, which can be typically located at a position that is suitable for loading and/or unloading sample container carriers, may be provided. Such an electromagnetic actuator may for example be pivotably embodied, in order to allow movement of the capsule for dispatch and/or in this case for example also turning of the conveying surfaces.

The driving unit may be designed for generating a positive and/or negative pressure in the tube, in order to move the capsule through the tube. This can correspond to an efficient possibility for moving such capsules through a tube, similar to a known pneumatic dispatch system. This can make it possible to fall back at least partially on known components. The driving unit may further have wheels, drag belts or the like.

The dispatching device may identify the capsule, whereby for example multiple capsules can be used in the dispatching device. In this way, the dispatching device can for example detect from which external position, that is to say for example from which receiving station, a capsule comes when there are a number of possibilities for this.

The capsule may secure closure, so that all possibly loose and/or open components can be checked for their state before the dispatch of the capsule. In this way it can be possible for example to avoid dispatching the capsule with an unclosed opening. Furthermore, the integrity of a sample can also be investigated on the basis of the device for securing closure, since in this way an undesired opening of the sample can be detected. This is useful, for example, whenever a defect occurs and a sample to be transported has to be removed from the system. It can then be possible to remove the sample at the defective location and feed it back in at another location. If the sample is opened, it can be considered to be compromised and is sent for disposal.

A sample distribution system can comprise a plurality of sample container carriers for receiving one or more sample containers. A sample container carrier can have at least one magnetically active element for interacting with a magnetic field generated by at least one electromagnetic actuator in such a way that a driving force on the sample container carrier can be brought about. The sample distribution system can also comprise a transport surface for carrying the sample container carriers and a plurality of electromagnetic actuators, which may also be referred to as transport surface actuators, arranged in a stationary manner under the transport surface. The electromagnetic actuators can move sample container carriers arranged on the transport surface by exerting a magnetic force on the sample container carrier. The sample distribution system can also comprise a dispatching device and a control device, which is designed for activating the electromagnetic actuators or transport surface actuators arranged under the transport surface in such a way that a respective sample container carrier moves on the transport surface along a predeterminable path of movement, activating the at least one electromagnetic actuator or conveying surface actuator arranged under the conveying surface and/or the electromagnetic actuators or transport surface actuators arranged under the transport surface in such a way that a sample container carrier is moved from the transport surface in the direction of the conveying surface or from the conveying surface in the direction of the transport surface, and activating the driving unit in such a way that the capsule is moved in the tube between the transport surface and the external position.

The plurality of electromagnetic actuators, also be referred to as transport surface actuators, can be arranged in a stationary manner under the transport surface may be distributed in the manner of a matrix, so that a two-dimensional movement over the transport surface can be brought about.

The advantages of a dispatching device can be made suitable for being used for a sample distribution system. In particular, sample container carriers can not only be moved on the transport surface, but can also be advantageously dispatched to an external position. It can thereby similarly be possible to dispense with manual interventions and also to dispense with complicated transporting mechanisms.

The sample container carriers that are moved from the transport surface in the direction of the conveying surface can typically be sample container carriers to be dispatched. The sample container carriers that are moved from the conveying surface in the direction of the transport surface can typically be dispatched sample container carriers. A dispatched sample container carrier can be understood as meaning a sample container carrier that has been inserted into the capsule at the external position and can be received on the transport surface for distribution.

By being moved along in the tube, the capsule can be brought into a position in which the conveying surface can form a level extension of the transport surface. This can be achieved for example by suitable stops. By such an arrangement of the conveying surface in relation to the transport surface, it can be possible to make sample container carriers move along from the transport surface onto the conveying surface, and vice versa, without obstacles such as for example offsets or slopes.

It can be understood that, given a corresponding configuration of the capsule and/or of the tube, the conveying surface can only form a level extension of the transport surface when corresponding openings in the tube or in the capsule have been opened. It may also be necessary first to bring a desired conveying surface into a position alongside the transport surface, for example by turning.

For the purpose of dispatching a sample container carrier located on the transport surface, the control device may be designed for activating the driving unit in such a way that the capsule can be moved into a loading position, in which the conveying surface forms a level extension of the transport surface, activating the electromagnetic actuators arranged under the transport surface in such a way that the sample container carrier to be dispatched can be moved on the transport surface to the capsule, activating the at least one electromagnetic actuator arranged under the conveying surface and/or the electromagnetic actuators arranged under the transport surface in such a way that the sample container carrier can be moved onto the conveying surface, and activating the driving unit in such a way that the capsule can be moved through the tube in the direction of the external position.

By such a design of the control device, automated dispatch of a sample container carrier with a sample container contained therein from the transport surface to the external position can be achieved in an advantageous manner.

The control device may be for example a computer, a microcontroller, a microprocessor, a programmable logic controller (PLC) or the like. The control device may have for example a processor and a memory. The memory can store program code that can cause the control device to behave in a defined way when it is executed.

For the purpose of receiving a sample container carrier located in the capsule, the control device may be designed for activating the driving unit in such a way that the capsule with the sample container carrier contained therein can be moved into a loading position, in which the conveying surface forms a level extension of the transport surface, and activating the electromagnetic actuators arranged under the transport surface and/or the at least one electromagnetic actuator arranged under the conveying surface in such a way that the sample container carrier can be moved onto the transport surface.

By such a design of the control device, receiving a sample container carrier with a sample container received therein from the external position can be achieved in an advantageous manner. For example, in this way samples can be received from an external analyzer, from a sample supplier, such as for example a receiving station, a hospital or some another sample source.

According to a development, the sample distribution system can have a further transport surface at the external position, which can be designed for carrying sample container carriers, and also can have a plurality of further electromagnetic actuators arranged in a stationary manner under the further transport surface. The further electromagnetic actuators can move sample container carriers arranged on the further transport surface by exerting a magnetic force on the sample container carrier. The dispatching device can dispatch a sample container carrier from the transport surface to the further transport surface and/or from the further transport surface to the transport surface.

Two spatially separate transport surfaces can be connected to one another, so that an exchange of sample container carriers with sample containers contained therein can be possible. This can make possible a considerable increase in flexibility when setting up a sample distribution system.

The control device may activate the electromagnetic actuators arranged under the further transport surface in such a way that a sample container carrier can be moved on the transport surface along a predeterminable path of movement. In this way, it can be possible for the further transport surface to be used in a way similar or identical to the transport surface, and moreover for it to be controlled by the same control device.

The further transport surface may for example be located in a different room, so that it can be possible for the sample distribution system to be split between a number of rooms, a number of floors, a number of buildings or the like.

The transport surface may be divided into logical zones, each logical zone being respectively assigned an electromagnetic actuator from the plurality of electromagnetic actuators or from the plurality of further electromagnetic actuators, the conveying surface of the capsule forming a further logical zone, and the control device handling the logical zone that is formed by the conveying surface as a logical zone of one of the transport surfaces when the conveying surface forms a level extension of the respective transport surface. In this way it can be possible to achieve a simple implementation of the internal procedures in the control device, since the control device does not have to take into account a separation between the transport surface and the conveying surface with regard to the activation of the electromagnetic actuators.

It should be understood that alternative mechanisms may also be used for the transfer from the transport surface into the capsule, i.e. for bringing a sample container carrier with sample containers received therein from the transport surface onto the conveying surface, and vice versa. For example, a gripping arm, a drag belt or some other device for moving the transport device may be used for this. Embodiments of a dispatching device and of a sample distribution system that use such a mechanism, that is to say in particular a gripping arm or a drag belt, instead of an electromagnetic actuator may be understood as independent concepts. With regard to further details of these concepts, reference can be made to the embodiments given above, as long as they are compatible with the use of a gripping arm, a drag belt or some other mechanism.

The laboratory automation system can have a number (for example between two and twenty) of pre-analytical and/or analytical and/or post-analytical stations for working on or processing sample containers and/or samples that are contained in the sample containers. The working or processing may for example comprise reading a barcode, removing a cap on the tube, centrifuging the sample, aliquoting the sample, analyzing the sample, etc. The laboratory automation system can further have a sample distribution system for transporting the sample containers between the pre-analytical, analytical and post-analytical stations.

The pre-analytical, analytical and post-analytical stations may for example have at least one station from the group of following stations: a cap-removing station for removing caps or closures on sample tubes, a cap-applying station for applying caps or closures to sample tubes, an aliquoting station for aliquoting samples, a centrifuging station for centrifuging samples, an archiving station for archiving samples, a pipetting station for pipetting, a sorting station for sorting samples or sample tubes, a sample-tube-type determining station for determining a type of sample tube and a sample-quality determining station for determining the quality of a sample.

Figure 1:
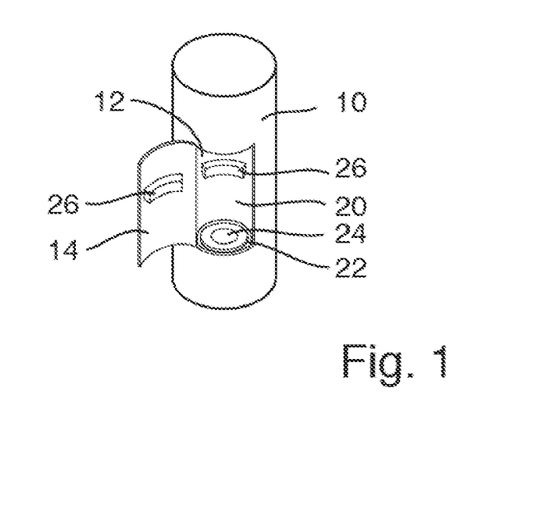
FIG. 1 illustrates schematically a capsule according to a first embodiment of the present disclosure.

Referring initially to FIG. 1, FIG. 1 shows a capsule 10 according to a first exemplary embodiment. The capsule 10 can dispatch sample container carriers with sample containers received therein, for example by a dispatching device.

The capsule 10 can have an opening 12, which can be closed by means of a flap 14. In FIG. 1, the flap 14 is shown in an opened state, so that the opening 12 can also be open. As a result, an interior space 20 of the capsule 10 can be accessible.

On an underside of the interior space 20, there can be a conveying surface 22, on which a sample container carrier can be received. Arranged underneath the conveying surface 22 can be an electromagnet 24, by which a force can be exerted on the sample container carrier, which can include a magnetically active element in the form of a permanent magnet.

The interior space 20 can be embodied in the form of a cylinder. In order to fix a sample container carrier and a sample container contained therein better in the capsule 10 during transport, the capsule 10 can have in the interior space 20 a holding device in the form of two jaws 26. In this way, tipping over or skidding around of a sample container in the capsule 10 can be avoided.

Figure 2:
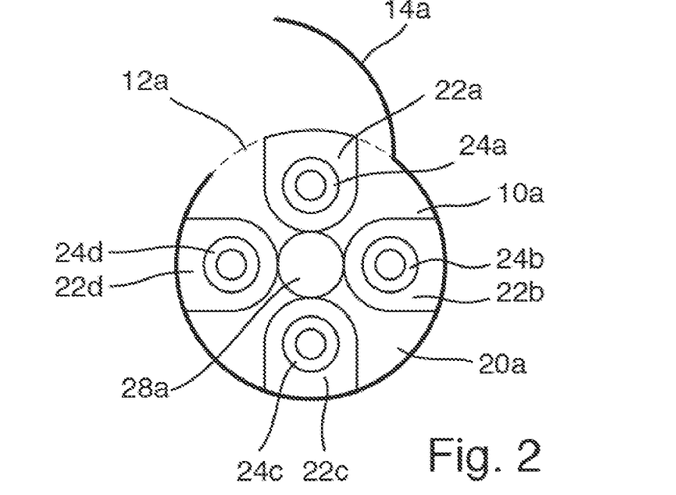
FIG. 2 illustrates schematically a capsule according to a second embodiment of the present disclosure.

FIG. 2 shows a capsule 10a according to a second exemplary embodiment, which is modified in comparison with the first exemplary embodiment to the extent that the capsule 10a according to the second exemplary embodiment has not just a single conveying surface for receiving sample container carriers with sample containers contained therein, but altogether four conveying surfaces 22a, 22b, 22c, 22d. Consequently, altogether four sample container carriers with sample containers contained therein can be transported at the same time in the capsule 10a.

Each of the four conveying surfaces 22a, 22b, 22c, 22d can have an electromagnet 24a, 24b, 24c, 24d respectively arranged under it, so that, by these electromagnets 24a, 24b, 24c, 24d, a force can be respectively exerted on a sample container carrier with a magnetically active element.

The capsule 10a according to the second exemplary embodiment can have an opening 12a, which can be closed by means of a flap 14a. The flap 14a is shown here in an opened state. By the opening 12a, an interior space 20a of the capsule 10a can be accessible.

Through the opening 12a, only one of the four conveying surfaces 22a, 22b, 22c, 22d can be accessible in each case. To be able to select which of the four conveying surfaces 22a, 22b, 22c, 22d can be accessible, arranged centrally in the interior space 20a of the capsule 10a can be an electric motor 28a, by which the four conveying surfaces 22a, 22b, 22c, 22d in the interior space 20a can be moved along a circular path. Consequently, a desired conveying surface of the four conveying surfaces 22a, 22b, 22c, 22d can be arranged in such a way that it can be accessible through the opening 12a when the flap 14a has been opened.

Figure 3A:
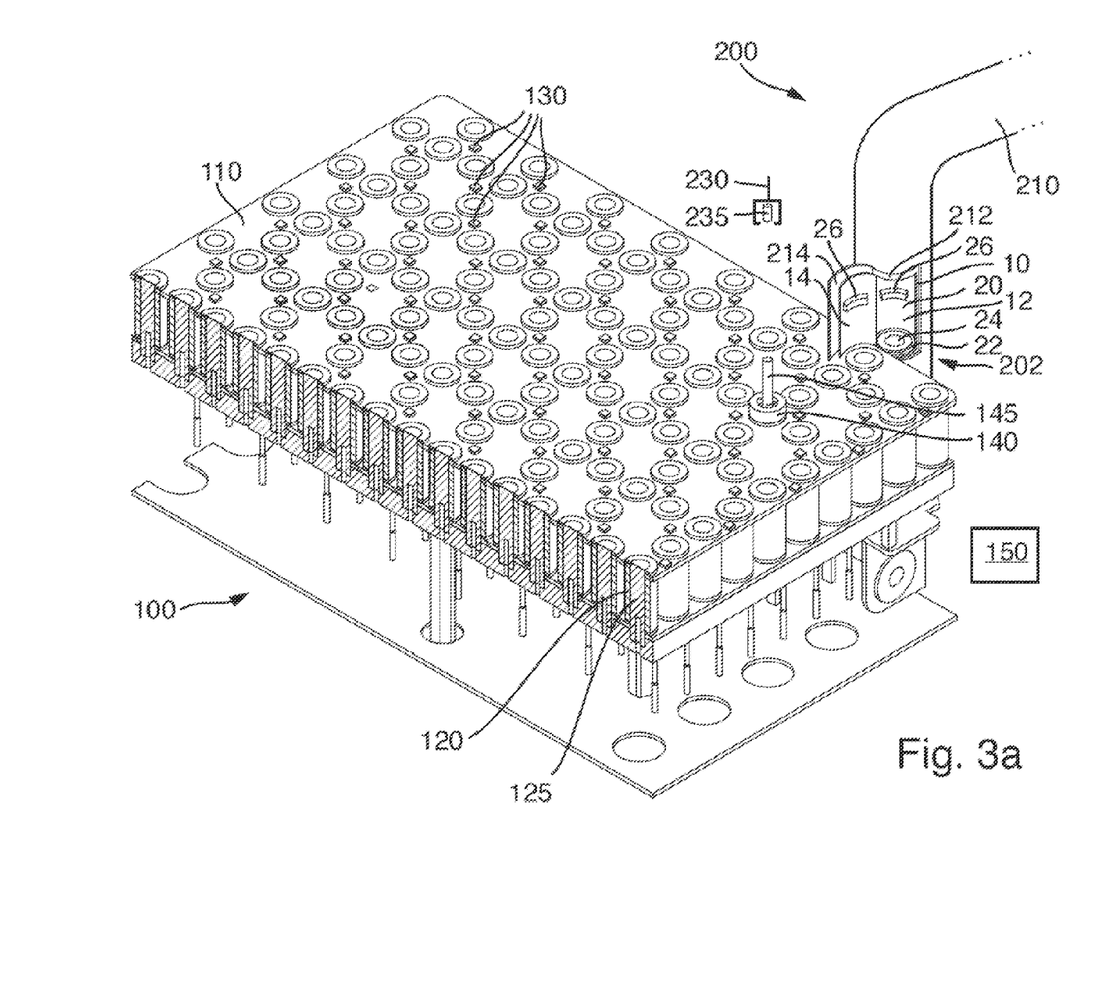
FIGS. 3a-b illustrate schematically a sample distribution system with a dispatching device according to an embodiment of the present disclosure.
Figure 3B:
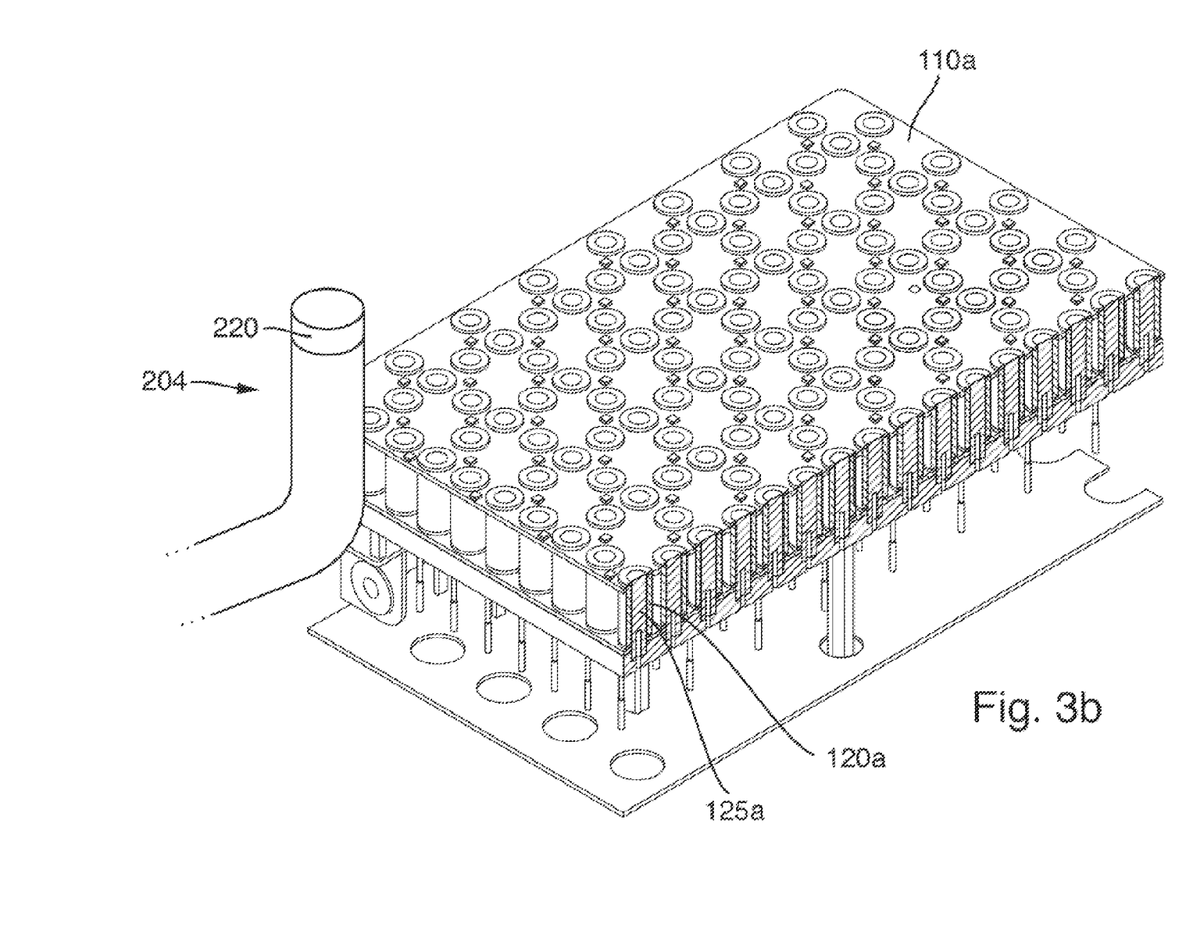

FIGS. 3a and 3b show a sample distribution system 100 with a dispatching device 200. The sample distribution system 100 can have two spatially separate transport surfaces 110 and 110a, which can provide level surfaces for the two-dimensional transport of sample container carriers 140. Shown here on the transport surface 110 can be a sample container carrier 140 with a sample container received therein in the form of a sample tube 145 embodied in the manner of a test tube. It can be understood that, in principle, any desired number of sample containers 145 may be arranged on the transport surfaces 110 and 110a and that they can move on the transport surfaces 110 and 110a.

For driving the sample container carrier 140, a plurality of electromagnetic actuators in the form of electromagnets 120 and 120a with respective cores 125 and 125a can be arranged under the transport surface 110 and 110a, respectively. These actuators can be individually activatable, so that they can generate magnetic fields in a defined way. In the sample container carrier 140 there can be a magnetically active element in the form of a permanent magnet, so that the sample container carrier 140 can be moved on the transport surface 110 or 110a by a magnetic field generated by the electromagnets 120 or 120a, respectively.

Also arranged on the transport surface 110 or 110a can be a number of position sensors in the form of Hall sensors 130, by which the position of the sample container carrier 140 on the transport surface 110 or 110a can be detected.

The sample distribution system 100 further can have a transport device 200. This device can have a tube 210, and can consequently be formed in a way similar to a pneumatic dispatch system. The tube 210 can connect a first position 202, which can be defined on the transport surface 110, to a remote position 204.

Provided in the tube 210 can be an opening 212, which can be closed by a flap 214. The flap 214 is shown here in an opened state, so that an interior space of the tube 210 can be accessible.

In the tube 210, there can be a capsule 10 according to the first exemplary embodiment that is represented in FIG. 1. Here, the flap 14 of the capsule 10 can also be opened, so that the opening 12 of the capsule 10 can likewise be open. The interior space 20 of the capsule 10 can consequently be accessible.

In the state shown in FIG. 3a, the conveying surface 22 can form a level extension of the transport surface 110. This can mean that a sample container carrier 140 can be moved from the transport surface 110 onto the conveying surface 22 and from the conveying surface 22 onto the transport surface 110 without obstacles.

At the opposite end of the tube 210, a driving unit 220 can be formed. The driving unit 220 can be suitable for generating a negative or positive pressure in the tube 210, so that a negative or positive pressure can prevail in the tube 210 on one side of the capsule 10. The capsule 10 can have in this case been received in the tube 210 in a sufficiently sealed manner, so that it can be moved through the tube by this negative or positive pressure. This can make it possible to move the capsule 10 back and forth between the first position 202 and the remote position 204 in the same way as in the case of a pneumatic dispatch system.

Furthermore, the dispatching device 200 can have a gripper 230, which in FIG. 3a is merely represented schematically. Here, the gripper 230 can grip a closure plug 235, which can be used for closing the sample container 145 before the dispatch of a sample container carrier 140 with a sample container 145 received therein. For this purpose, the closure plug 235 can be fitted onto the top of the sample container 145. The gripper 230 and the closure plug 235 together can form a closing device.

The remote position 204 can be formed alongside the further transport surface 110a, the two transport surfaces 110 and 110a being a spatial distance apart. This can mean for example that a direct transfer of a sample container carrier 140 from the transport surface 110 to the further transport surface 110a may not be possible.

The sample distribution system 100 further can have an electronic control device 150. The electronic control device 150 can have a processor and a program memory, the program memory containing program code that controls the behavior of the processor.

The electronic control device 150 can activate the electromagnets 120, 120a and the driving unit 220. It can furthermore open and close the flap 14 of the capsule 10 and the flap 214 of the tube 210. In addition, it can actuate the gripper 230. By use of the Hall sensors 130, the control device 130 can receive a check-back indication concerning the position of the sample container carrier 140.

The control device 150 can be capable of moving the sample container carrier 140 over the transport surface 110 or 110a by suitable activation of the electromagnets 120 or 120a, respectively. If the sample container carrier 140 with the sample tube 145 contained therein is to be sent from the transport surface 110 to the further transport surface 110a, the control device 150 can move the sample container carrier 140 into a position alongside the conveying surface 22. It can then actuate the gripper 230 in such a way that the sample tube 145 can be closed with the closure plug 235. In this way, a sample contained in the sample tube 145 can be protected against leakage. Subsequently, the control device 150 can activate the electromagnets 120 and the electromagnet 24 contained in the capsule 10 in such a way that the sample container carrier 140 can be moved onto the conveying surface 22. In other words, the sample container carrier 140 with the sample tube 145 received therein can be moved into the capsule 10. The sample tube 145 can be in this case stabilized laterally by the holding device 26.

Subsequently, the control device 150 can bring about closing of the two flaps 14, 214 and actuate the driving unit 220 in such a way that a negative pressure can be produced in the tube 210 above the capsule 10. This can draw the capsule 10 in the direction of the remote position 204. There, corresponding flaps, which are not represented in FIG. 3b, can be opened and the sample container carrier 140 with the sample container 145 contained therein can be transferred by the electromagnets 120a to the further transport surface 110a. On the further transport surface 110a, the sample container carrier 140 with the sample container 145 contained therein can be moved in the same way as on the transport surface 110.

It can be understood that, instead of the further transport surface 110a, at the remote position 204 there may also be provided an analyzer, to which a sample container carrier 140 with a sample container 145 received therein can be brought. Similarly, it can be understood that the same procedure can also be performed in reverse, i.e. for example a sample container carrier 140 with a sample container 145 contained therein can be dispatched from the further transport surface 110a to the transport surface 110.

The sample distribution system 100 can be a component part of a laboratory automation system with a number of pre-analytical, analytical and post-analytical stations that are not represented any more specifically and are arranged alongside the transport surfaces 110 and/or 110a. The sample distribution system 100 can serve for transporting the sample containers between these stations.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A dispatching device for dispatching sample containers received in sample container carriers from a transport surface of a sample distribution system to an external position with respect to the transport surface and/or from the external position to the transport surface, wherein a sample container carrier comprises at least one magnetically active element to interact with a magnetic field generated by at least one electromagnetic actuator such that a driving force is applied to the sample container carrier, the dispatching device comprises:
   a hollow tube adjacent to the transport surface, wherein the tube extends from a first position on the transport surface to the external position;
   a capsule movable within the hollow tube between the first position on the transport surface and the external position, the capsule comprising an interior space, wherein the interior space comprises a conveying surface level to the transport surface for receiving the sample container carrier within the interior space of the capsule, the capsule extends transversely in a longitudinal direction from the conveying surface;
   a driving unit to move the capsule within the tube between the first position on the transport surface and the external position, wherein the driving unit is located at the external position of the hollow tube; and
   at least one electromagnetic actuator arranged under the conveying surface of the capsule, the at least one electromagnetic actuator applies a magnetic driving force to the sample container carrier to move the sample container carrier into or out of the capsule.

2. The dispatching device according to claim 1, further comprises,
   a closing device comprising a gripper and a closure plug, wherein the closure plug is pressed onto the sample container by the gripper to close the sample container in the sample container carrier before the sample container carrier is introduced into the capsule.

3. The dispatching device according to claim 1, wherein the capsule comprises a holding device within the interior space of the capsule comprising two jaws to affix the sample container carrier with the sample container in the capsule.

4. The dispatching device according to claim 1, wherein the interior space of capsule comprises a plurality of conveying surfaces for transporting a plurality of sample container carriers through the hollow tube between the first position of the transport surface to the external position, wherein at least one electromagnetic actuator is arranged under each of the plurality of conveying surfaces.

5. The dispatching device according to claim 4, wherein the capsule comprises an electric motor to move the plurality of conveying surfaces in a circular path in order to bring one of the conveying surfaces in a specific level position suitable for loading and/or unloading.

6. A sample distribution system, the sample distribution system comprising:
   a plurality of sample container carriers for receiving one or more sample containers, wherein a sample container carrier comprises at least one magnetically active element to interact with a magnetic field generated by at least one electromagnetic actuator such that a driving force is applied to the sample container carrier;
   a transport surface to carry the sample container carriers;
   a plurality of electromagnetic actuators arranged in a stationary manner under the transport surface, wherein the electromagnetic actuators move sample container carriers that are arranged on the transport surface by applying a magnetic force to the sample container carriers;
   a dispatching device according to claim 1; and
   a control device to activate the electromagnetic actuators arranged under the transport surface such that a sample container carrier moves on the transport surface along a predeterminable path of movement, to activate the at least one electromagnetic actuator arranged under the conveying surface and/or the electromagnetic actuators arranged under the transport surface such that a sample container carrier is moved from the transport surface in the direction of the conveying surface or from the conveying surface in the direction of the transport surface, and to activate the driving unit such that the capsule is moved in the tube between the transport surface and the external position.

7. The sample distribution system according to claim 6, wherein by being moved in the tube, the capsule can be brought into a loading position in which the conveying surface forms a level extension of the transport surface.

8. The sample distribution system according claim 6, further comprising,
- a further transport surface at the external position to carry sample container carriers; and
- a plurality of further electromagnetic actuators arranged in a stationary manner under the further transport surface, wherein the further electromagnetic actuators move sample container carriers arranged on the further transport surface by applying a magnetic force to the sample container carriers, wherein the dispatching device dispatches a sample container carrier from the transport surface to the further transport surface and/or from the further transport surface to the transport surface.

9. A laboratory automation system, the laboratory automation system comprising:
- a plurality of pre-analytical, analytical and/or post-analytical stations to process sample containers and/or samples that are contained in sample containers; and
- a sample distribution system for distributing the sample containers between the pre-analytical, analytical and/or post-analytical stations, according to claim 6.

* * * * *